(12) United States Patent
Collins (10) Patent No.: US 8,691,066 B2
(45) Date of Patent: Apr. 8, 2014

(54) GAS SENSOR

(75) Inventor: Graham Collins, Hampshire (GB)

(73) Assignee: City Technology Limited, Portsmouth (GB)

( * ) Notice: Subject to any disclaimer, the term of this patent is extended or adjusted under 35 U.S.C. 154(b) by 1458 days.

(21) Appl. No.: 10/566,867

(22) PCT Filed: Aug. 12, 2004

(86) PCT No.: PCT/GB2004/003454

§ 371 (c)(1),
(2), (4) Date: Jul. 28, 2006

(87) PCT Pub. No.: WO2005/017518

PCT Pub. Date: Feb. 24, 2005

(65) Prior Publication Data

US 2007/0181423 A1    Aug. 9, 2007

(30) Foreign Application Priority Data

Aug. 13, 2003   (GB) .................................. 0319043.6

(51) Int. Cl.
    *G01N 27/413*    (2006.01)
(52) U.S. Cl.
    USPC ........... 204/432; 204/431; 439/271; 439/274; 439/587; 439/588; 439/272
(58) Field of Classification Search
    USPC ........... 204/421–432; 439/271–274, 587–588
    See application file for complete search history.

(56) References Cited

U.S. PATENT DOCUMENTS

| | | | | |
|---|---|---|---|---|
| 3,708,412 A | * | 1/1973 | Lofgren | 204/415 |
| 4,522,899 A | * | 6/1985 | Illmann et al. | 429/181 |
| 4,948,496 A | * | 8/1990 | Chand | 204/408 |
| 5,224,875 A | * | 7/1993 | Watanabe et al. | 439/587 |
| 5,234,567 A | * | 8/1993 | Hobbs et al. | 204/415 |
| 5,298,146 A | * | 3/1994 | Braden et al. | 204/406 |
| 5,662,336 A | * | 9/1997 | Hayashi et al. | 277/607 |
| 5,667,406 A | * | 9/1997 | Tabata et al. | 439/587 |
| 6,024,853 A | * | 2/2000 | Kiesele et al. | 204/412 |
| 6,638,107 B1 | * | 10/2003 | Silfverberg | 439/587 |
| 2003/0168336 A1 | * | 9/2003 | Downer et al. | 204/424 |
| 2004/0079637 A1 | * | 4/2004 | Maeno et al. | 204/431 |
| 2005/0179438 A1 | * | 8/2005 | Derr | 324/438 |
| 2006/0108223 A1 | * | 5/2006 | Derr | 204/433 |

FOREIGN PATENT DOCUMENTS

| | | |
|---|---|---|
| GB | 2 073 891 | 10/1981 |
| WO | WO 01/81911 | 11/2001 |
| WO | WO 02/088694 | 11/2002 |

* cited by examiner

*Primary Examiner* — Bach Dinh
(74) *Attorney, Agent, or Firm* — Husch Blackwell LLP

(57) ABSTRACT

A current collector wire (1) is over-moulded with a seal (2) made from a thermoplastic elastomer (Santoprene 64) having a (64) Shore A hardness rating. In a three electrode carbon monoxide sensor three current collector wire (1a, 1b, 1c) and seal (2a, 2b, 2c) combinations are inserted into the body (3) through receiving apertures (12a, 12b, 12c) in a side wall of the body, so that the current collectors protrude through connection apertures (12a, 12b and 12c). The outside diameters of the seals and the bores of the apertures are dimensioned to provide an interference fit of the one in the other. The seals are pressed home into receiving apertures in the body (3) to provide compression of the seals against both current collectors and the aperture bores resultant from the interference. Gold-plated phosphor bronze clips (8) are attached which locate on and are retained by barbs on the housing, thereby trapping the current collector wires and providing electrical contact to external circuitry.

19 Claims, 7 Drawing Sheets

GAS SENSOR

The present invention relates to a gas sensor, in particular an electrochemical gas sensor, and to a current collector and seal therefor.

In such a sensor at least a pair of electrodes is provided in contact with an electrolyte, whereby a potential develops between the electrodes. The potential varies with concentration of gas. The electrolyte is held captive in the sensor by a gas permeable, liquid impermeable membrane. The electrodes are typically not plates, but typically thin layers of gas diffusion catalyst pressed on to hydrophobic gas permeable backing tape and as such not easy to make contact with. Generally, it is desirable for contact to be made with them by thin connectors, known in the art as current collectors. These can be of wire or ribbon. Their thinness gives them at least partial ability to follow the surface shape of the electrodes.

Leading the current collectors outside the housing of a gas sensor in a reliable sealing manner is difficult and this invention relates to improvements in this respect.

Further technical requirements of current collectors are that:
they should have low electrical resistance and
they should be chemically inert to the electrolyte, which is aggressive, typically a high concentration acid.

Accordingly, it is most common to employ noble metal current collectors.

A number of approaches to the requirement for reliable sealing have been suggested, including the use of plastics material sensor housings with conductive portions, which press against peripheral regions of the electrodes, and the potting of electrode edges and emergent current collectors in epoxy or similar materials. However, in our opinion neither of these approaches offers a solution having adequate performance, reliability and ease of manufacture.

A better approach is described in GB 2094005. Here, the current collectors are small diameter wires or flattened ribbons of noble metal, interleaved with the gas diffusion electrodes and insulating separators in a stack arrangement which is wetted by electrolyte from a reservoir via a wick. The current collectors provide good contact across the electrode face, thereby ensuring efficient cell performance, and emerge from the stack where the gas porous backing material of two or more of the electrodes is brought into contact in a peripheral annular zone. By arranging for adequate pressure to be applied in this region (for example via an O-ring at the top of the stack which is compressed on assembly of the housing), an electrolyte-tight seal may be produced. The performance of this seal relies on the ability of the electrode backing material (typically PTFE) to creep under pressure and so form itself around the current collector. Thus, gas is able to diffuse in to the active region, but electrolyte is contained by the hydrophobic properties of the electrode backing tapes and the annular seal.

Commercial experience over many years has shown that current collector seals fabricated as described in GB 2094005 are capable of high levels of performance, but has also highlighted a number of difficulties:

1. The manufacturing process is difficult to automate due to the complexity of the assembly, especially in systems employing multiple electrodes and so requiring several current collectors. A number of steps must be completed simultaneously; (a) alignment of multiple current collector ribbons, (b) alignment of two or more electrode backing tapes, (c) ultrasonic or other closure of the outer sensor casing to produce adequate pressure in the seal area;

2. There are difficulties in implementing such designs in sensors having significantly reduced dimensions due to manual handling complexities and the need for an adequate seal length (i.e. the footprint of the annular seal zone needed to ensure integrity throughout the sensor life);

3. The design of these sensors demands that the seal design perform a number of functions. It must retain an aggressive liquid electrolyte over a period of years whilst subject to significant fluctuations in temperature, humidity and other environmental factors. Simultaneously, it must not compromise the mechanical or electrical integrity of the current collectors passing through it. It must also maintain the relative positions of the electrodes and current collectors without allowing any movement which could compromise the cell performance in any orientation. Therefore, optimal performance in any one aspect is usually obtained at the expense of behaviour which is compromised in other respects.

Whilst rigid current collectors are not favoured in sensor designs of the type described in GB 2094005, electrochemical gas sensor designs based around robust, inflexible current collectors are feasible. Typically these rely on an O-ring seal of the type described in WO-A-01/81911 to retain the electrolyte. However, when attempting to miniaturise sensors and use smaller pins and O-rings, the seal length (i.e. the length of pin and sensor housing in contact with the inner and outer surfaces of the O-ring) becomes rather small and this may compromise the overall integrity of the design. Furthermore, the features required in the housing in order to produce compression of the O-ring occupy valuable space and further mitigate against attempts to miniaturise the arrangement. The stress which almost inevitably exists within the sensor housings in such circumstances is also a potential source of failure, particularly as the device experiences thermal transients during its life. These problems are common to many types of gas sensor, and although some partial solutions have been proposed, difficulties remain. Such problems are greatly exacerbated when seeking to significantly reduce the size of sensors to meet the demands of instrument manufacturers.

A further difficulty in prior gas sensors is that relatively fragile current collectors have not been seen as a suitable means of making electromechanical contact of the sensor in a rugged industrial environment where repeated insertions into sockets may be required over the life of the sensor. It is therefore common to join a flexible current collector to a lower cost pin, pad or other conventional connection means in a region of the housing where no electrolyte contact will occur. A double skin sensor wall construction may also be employed to provide further protection of the current collector as it travels from the seal to the external connection means.

The object of the present invention is to provide improve sealing in gas sensors.

In accordance with a first aspect of the present invention, we provide a current collector and seal combination for an electrochemical sensor having a housing, in which are located sensing and counter electrodes in contact with a liquid electrolyte, and connection apertures in a wall of the housing, the current collector and seal combination including:
a flexible current collector adapted for direct contact with one of the sensor's electrodes and
a compliant seal adapted to fit in the one of the connection apertures, the current collector extending through the compliant seal,
the seal being in contact with the collector substantially throughout its length along the current collector and
the seal being of an elastomeric material, the arrangement being such that compressive stress induced in the seal by reaction from the connection aperture urges the seal into distributed sealing contact with the current collector substantially throughout the length of the seal.

According to a second aspect of the invention, we provide an electrochemical gas sensor having:

a housing having at least one wall and a plurality of connection apertures through the said wall, the apertures having bores, sensing and counter electrodes housed in the housing, a liquid electrolyte contained in the housing in chemical contact with the electrodes and a plurality of current collectors in electrical contact with respective ones of the respective electrodes;

characterised in that:

the plurality of current collectors are in combination with a corresponding plurality of compliant seals in accordance with the first aspect of the invention; in that the current collectors extend within their seals through respective ones of the apertures from their electrodes to outside the housing; and in that the compliant seals are in compression against both their current collectors and the bores of their apertures, whereby the current collectors provide means for electrical contact outside the housing and the apertures are sealed.

By "compliant seal" we mean a seal of a material that is softer than materials normally regarded as rigid and in particular that the seal is softer than the material of the housing, bearing in mind that all materials have a hardness, including rigid materials. The concept of a compliant seal includes that the housing maintains the compressive stress in the seal, due to its relative rigidity. In more specific terms, the compressive stress is liable to be at a level inducing significantly more strain in the seal than in the housing, in which the strain will be small in comparison to that which would appertain at the elastic limit of the housing material.

Normally the ratio of elastic modulii of the housing and the seal will differ by at least two orders of magnitude.

Provision of contact between the seal and the current collector throughout the length of the seal provides for enhanced sealing against aggressive electrolytes, which have a recognised ability to permeate along material discontinuities, e.g. track along any gap between the current collector and the seal. By contrast, an O-ring has a contact zone, which is short in comparison with the length of the O-ring, i.e. its dimension normal to the central plane of its annulus.

It should be noted that although elastomeric seals, e.g. O-rings, are commonplace, the use of elastomer in the invention is important in providing that the seal material is resistant to stress-relieving creep. In other words, the compressive stress giving efficacy to the seal is maintained through the life of the sensor. Although it is conceivable that the elastomer could be conventionally moulded of thermosetting rubber, the preferred seal is of thermoplastic elastomer moulded by an injection process.

We have considered a number of methods whereby the current collector/seal assembly may be fabricated as a subassembly ready for incorporation into sensors as described above.

(1) A central mandrel may be inserted into the mould and then withdrawn afterwards in order to create the central aperture. There is also the possibility of drilling through a solid seal in order to create the aperture. Mechanical drilling of compliant materials presents many difficulties, and laser drilling is probably a better option, although the high aspect ratio of the aperture may present problems. Whatever method is selected to preform the seal, it is then necessary to thread the current collector through the central aperture so that the seal provides an interference fit to the wire in the completed assembly. But since noble metal wires of diameters in the 100 micron range offer relatively little resistance to buckling stresses and the length of the aperture is of the order of mm, this process is difficult. Overall, therefore, although the production of seals which are subsequently threaded with current collectors is possible, it does not offer an optimum, simple low cost route to the production of this key assembly.

(2) The much preferred solution is to over-mould the seal directly on to the current collector, for example by injection moulding. Alternatively, a range of casting or "dough moulding' methods may be employed. The required aperture dimensions are automatically provided and suitable choice of seal material ensures that no damage occurs to the current collector during the process. A further advantage is that multiple seals may be created at suitable spacings on a length of current collector in a single moulding process. In yet a further enhancement, we envisage repeating this process on a continuous length of current collector wire which is automatically incremented or indexed through the mould when it opens at the end of each run. Thus, one may produce a reel of current collector material with appropriately spaced seals mounted thereon which can in turn be used to feed an automated assembly machine in the sensor production process.

3) It would also be possible to over-mould the current collector seal after the current collector has been located within the exit port of the sensor housing. The wire must be (at least) temporarily retained in position relative to the opening or port. Although accurate positioning of such a thin wire in a relatively large opening presents challenges, one favoured approach would be to over-mould at least part of the relatively hard sensor casing around the current collector wire itself in a first shot. (This would not produce a satisfactory long term seal for the sensor due to the mismatch in properties between the current collector and the casing—which the seal is designed to accommodate—but would certainly provide good retention of the current collector whilst the remaining assembly processes took place.) Subsequently, the current collector seal would be formed by "back-filling" by a second shot of TPE. This technically sophisticated approach offers significant further reductions in labour required in the overall assembly process.

Taking into account the conflicting demands of lower cost, the desire for increased automation of sensor assembly and the practical difficulties of the various approaches, the method (2) is currently seen as the most favourable and the example described below is based on this approach.

As an alternative to moulding with a through-bore, the seal could be moulded with a slot, nick or notch, into which the current collector can be introduced prior to insertion of the seal into its housing aperture, compression of the seal serving to seal the slot etc. The slot can be extended past the intended position of the current collector to close to the side of the current collector opposite from the opening of the slot in a "clam shell" arrangement. In another alternative, the seal can be moulded in two halves with complementary locating formations. In both the alternatives, it is preferable to provide a slight indent for correct centring of the current collector in the seal.

Where the natures of the seal and the current collector permit, it can be envisaged that the seal is bonded to the current collector. However, the latter is likely to be too smooth for bonding to occur in moulding. Sliding of the seal along the current collector prior to fitting is not expected to provide a leak path, in view of the compression of the seal in use.

Where the seal is moulded prior to fitting, its compression can be achieved by providing an interference fit with the bore of the connection apertures. An interference fit implies that that the connection aperture diameter is slightly smaller than the relaxed diameter of the seal; the compliant nature of the seal allows insertion to take place without any damage to the current collector passing through the centre. Once insertion is complete, however, the elastomeric properties of the seal produce significant sealing forces which act to force the housing/seal and the seal/current collector surfaces into intimate contact. These forces, applied along the length of contact of the seal with the current collector, provide a high integrity seal against electrolyte leakage, even when using liquids which have the ability to 'track' along small apertures.

The physical dimensions of the seal are dictated as much by the physical constraints on the material as by optimisation of the performance of the seal, in that the seal will normally be as small as feasibly possible given the need to be able to handle/manipulate, by hand or machine, the current collector and to mould the seal.

It is envisaged that the minimum diameter current collector is 0.025 mm; whilst the maximum diameter is likely to be 0.3 mm. Smaller wire is very fragile and larger wire is difficult to work with. In practice, 0.1 mm is the preferred diameter of the wire.

The minimum size, i.e. overall dimension in any direction, that we can conveniently mould is 1.0 mm or just less. Thus with the preferred current collector wire and a minimum sized moulding, the ratio of the length of the seal to the diameter of the wire is of the order of 10:1. Similarly the ratio of the seal and wire diameters is also of the order of 10:1. If the wire is size is reduced to minimum, the ratios could be of the order of 40:1. If the seal dimensions are increased for the same size wire the ratio also increases, for instance the preferred embodiment seal is 3 mm long, giving a ratio of 30:1 for length and 12:1 for diameter. The only case where the ratio would be significantly below 10:1 is the unusual case where the wire diameter is greater than 0.1 mm and the seal is of minimum size.

The seal can be longer than its diameter (or other major cross-sectional dimension) and typically is so. Thus the ratio of the seal length to diameter is typically greater than 1:1 and normally of the order of 3:1 at least.

A long seal may be used to create a number of zones of higher compression stress along the length of the seal. For example, by providing the body of the seal with a ridged structure, the sealing forces generated following insertion into the connection aperture may be enhanced in a series of laterally spaced annular zones. Control of the seal and housing dimensions and construction materials ensure that excessive forces, unsupportable by the current collector passing through the centre, are not produced. Such a ridged, or sawtooth construction may also assist in the insertion of the seal, as the tolerance demands upon the connection aperture are somewhat relaxed in comparison with the situation which exists when a smooth bore approach is employed.

Even when the seal is provided with high compression zones, by increasing its local diameter, it will normal be of circular cross-section. However, it can be imagined to be provided with non-circular, but regular cross-sectional shape.

Additional longitudinal compression of the seal may also be used in order to generate the additional sealing forces. For example, a longitudinal extension of the seal may be compressed after insertion using a clip which locates over the external moulded sensor housing. This approach may be employed even if the receiving aperture is marginally larger than the seal. This technique is useful in setting up compression in a back-filled seal, where no interference induced compression is present.

To help understanding of the invention, a specific embodiment thereof will now be described by way of example and with reference to the accompanying drawings, in which.

Figure 1A:
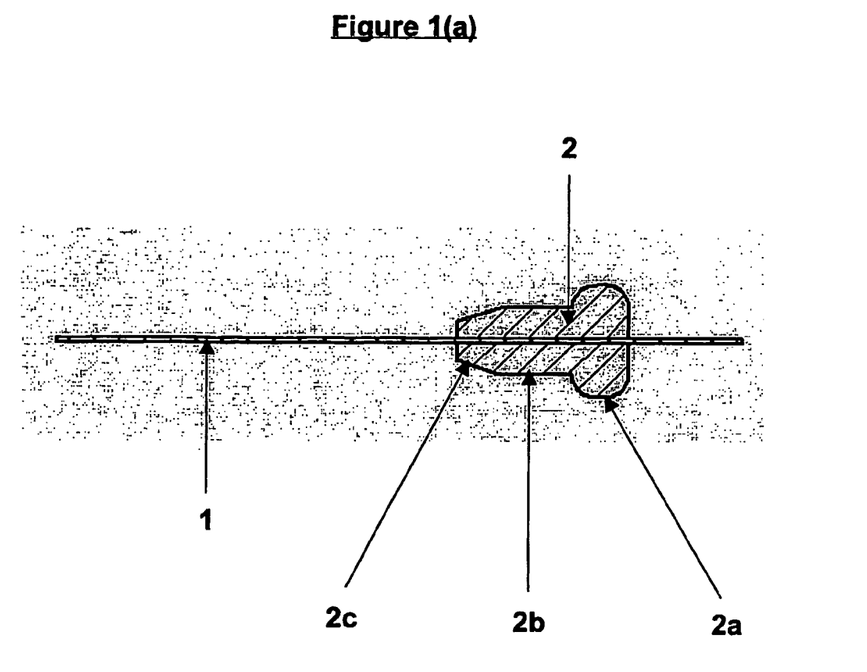
FIGS. 1(a) and 1(b) are a longitudinal section and isometric view respectively of a current collector and seal assembly.
Figure 1B:
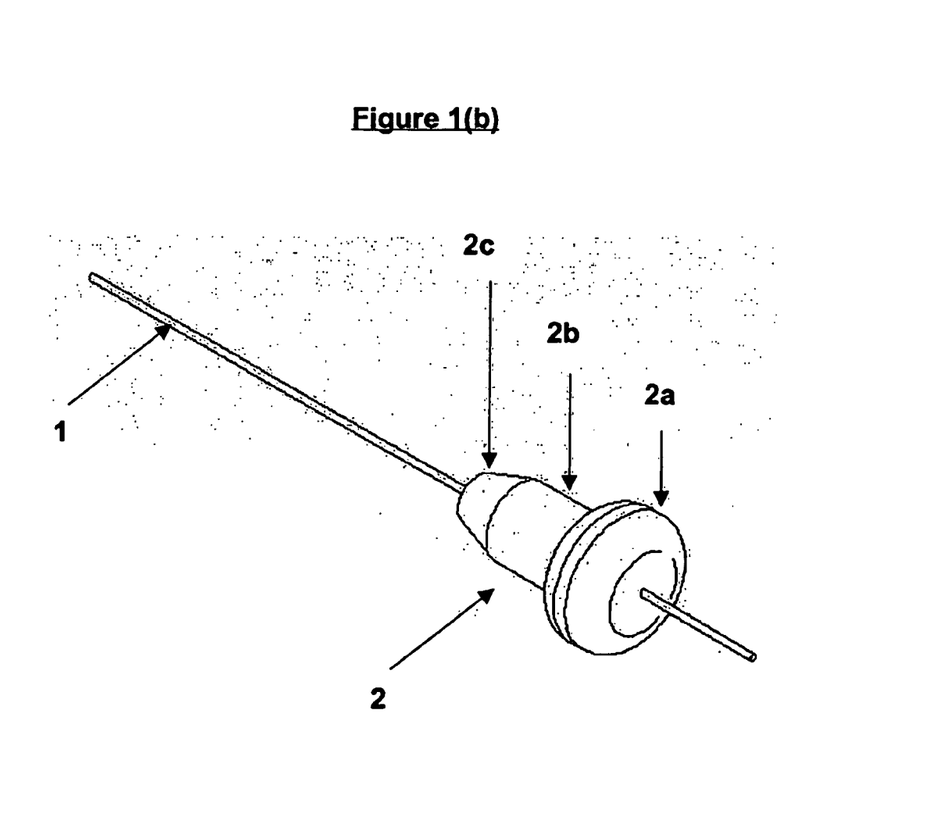

FIGS. 1(a) and 1(b) show a 0.1 mm/100 micron diameter current collector wire 1 (platinum for a carbon monoxide sensor or nickel for an oxygen sensor) over-moulded with a seal 2 made from a thermoplastic elastomer (Santoprene 64) having a 64 Shore A hardness rating. The over-moulding was performed in a four cavity mould tool which simultaneously produced four such seals along the wire 1 at a pitch of 16 mm. The current collector wire 1 may be fed into the mould tool under tension from a continuous reel arrangement, although in this case a length was cut from the reel and tensioned using appropriate weights. After removal from the mould tool, the assembly was diced to produce 4 identical over-moulded current collectors of the type shown in FIG. 1. The overall length of the seal is 3.0 mm, comprising an outer end boss 2a (11.0 mm long×2.0 mm diameter), a cylindrical body 2b (1.24 mm long×1.2 mm diameter) and a tapered nose 2c (0.76 mm long, narrowing to 0.7 mm diameter). Further manufacturing details of these seal/current collector combinations will be within the ability of the man skilled in the art.

Figure 2:
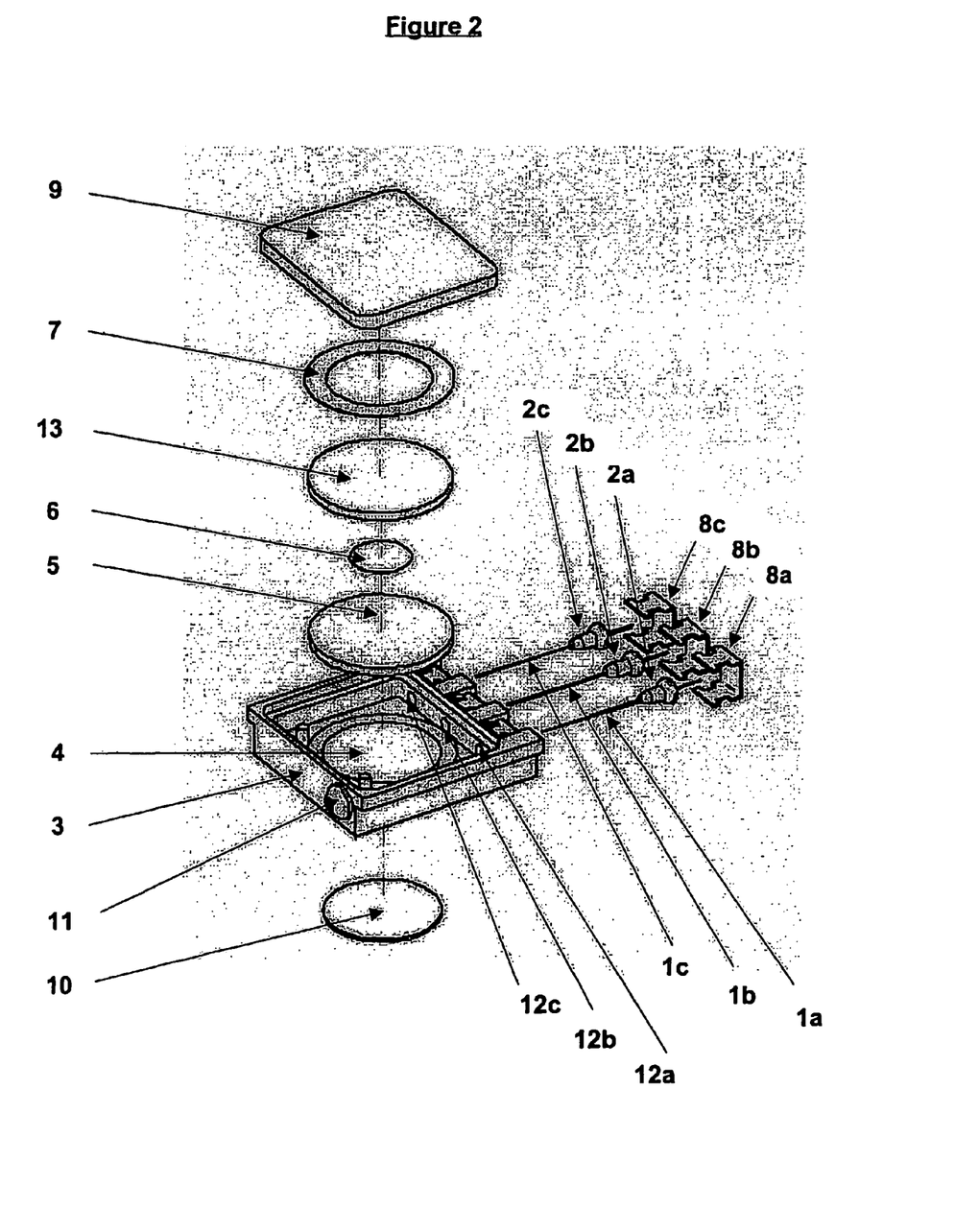
FIG. 2 is an exploded view of a first example of a sensor.

The use of these current collectors in the assembly of a three electrode carbon monoxide sensor is shown in FIG. 2. A sensing electrode 4 is of conventional construction and comprises a gas diffusion catalyst (typically high surface area platinum) pressed on to a 12 mm diameter hydrophobic gas permeable backing tape, typically of PTFE. This is heat sealed into a sensor housing or body 3 around the perimeter of the backing tape so that the electro-catalyst is uppermost in the orientation shown in FIG. 2. If required, filter cloth(s) or suitably packaged filter powder(s) may be trapped between the sensor housing and the electrode. The body 3 is provided with a suitable gas diffusion barrier in the centre of the region covered by the electrode 4, in this case a capillary with diameter 0.8 mm. Both the body 3 and a back plate 9 are injection moulded from the thermoplastic ABS material "Cevian V660'.

The relative elastic modulii of the thermoplastic elastomer of the seal and the ABS material of the body are 10.43 MPa for Santoprene 64 TPE and 2500 MPa for Cevian V660 ABS. This shows a 239:1 ratio between elastic modulii.

Three current collector wire 1a, 1b, 1c and seal 2a, 2b, 2c combinations of the type shown in FIG. 1 are inserted into the body 3 through receiving apertures 12a, 12b, 12c in a side wall of the body, so that the current collectors protrude through connection apertures 12a, 12b and 12c. The outside diameters of the seals and the bores of the apertures are dimensioned to provide an interference fit of the one in the other. This can be achieved by fine tuning the injection moulding parameters—injection pressure, packing, shot size, etc. The seals are pressed home into receiving apertures in the body 3 to provide compression of the seals against both current collectors and the aperture bores resultant from the interference. Next, gold-plated phosphor bronze clips 8 are attached which locate on and are retained by barbs on the housing, thereby trapping the current collector wires and providing electrical contact to external circuitry. The clips 8 also provide a degree of longitudinal compression of the seal, thereby increasing the compressive stress and sealing effect between the seal, body and current collector. Optionally, the section of wire 1 which protrudes through the seal 2 on the outside of the sensor body 3 may be spot welded to clip 8 before attachment to provide greater robustness in the connection. The current collectors for the reference and counter electrodes are then bent up into a vertical direction, allowing the remainder of the electrode stack to be assembled in a conventional interleaving fashion.

A porous glass wool separator 5 (12 mm diameter) is placed over the sensing electrode 4, so trapping the sensing current collector between the two. A 6.7 mm diameter reference electrode 6 (fabricated in an analogous way to the sensing electrode 4) is then placed in the centre of separator 5 (again with the electro-catalyst facing upwards in the Figure). The associated current collector is bent down from its vertical position to make contact therewith, before a second 12 mm diameter separator 13 is laid on top, trapping the current collector in place. The third (counter) current collector is then brought down to a horizontal position before a conventional gas diffusion annular counter electrode 7 (internal/external diameters 6.7/11.5 mm) completes the stack. The sensor back plate 9 is then located into a mating recess in body 3 before being ultrasonically welded into position, thereby achieving a liquid-tight seal and producing the required degree of compression on the electrode stack to give good electrical contact throughout the assembly. Electrolyte (0.15 ml of 5M sulphuric acid) is then injected into the housing through a filler port 11 which is then closed by heat-taking. After attaching a gas permeable bulk flow membrane 10 to the front of the body 3, the sensor is then tested and prepared for dispatch to the customer.

Figure 3:
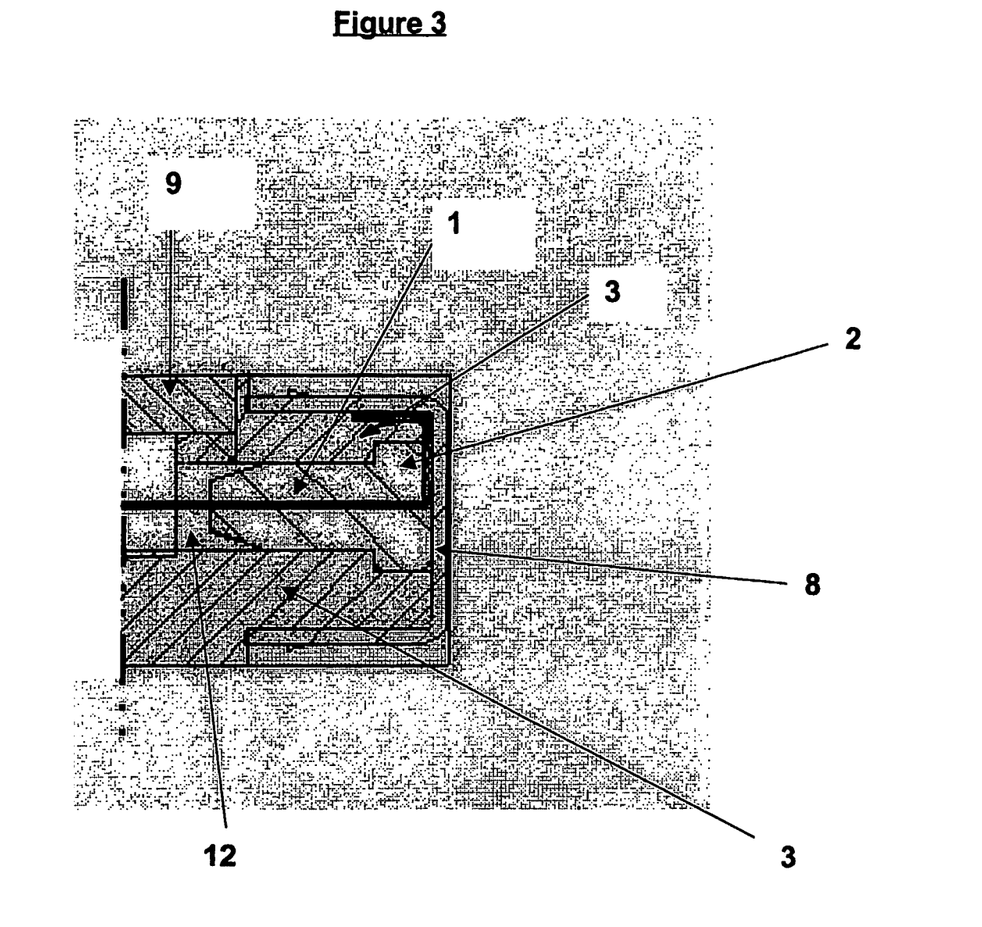
FIG. 3 is a cross-section through a seal and current collector located in the sensor housing apparatus.
Figure 4:
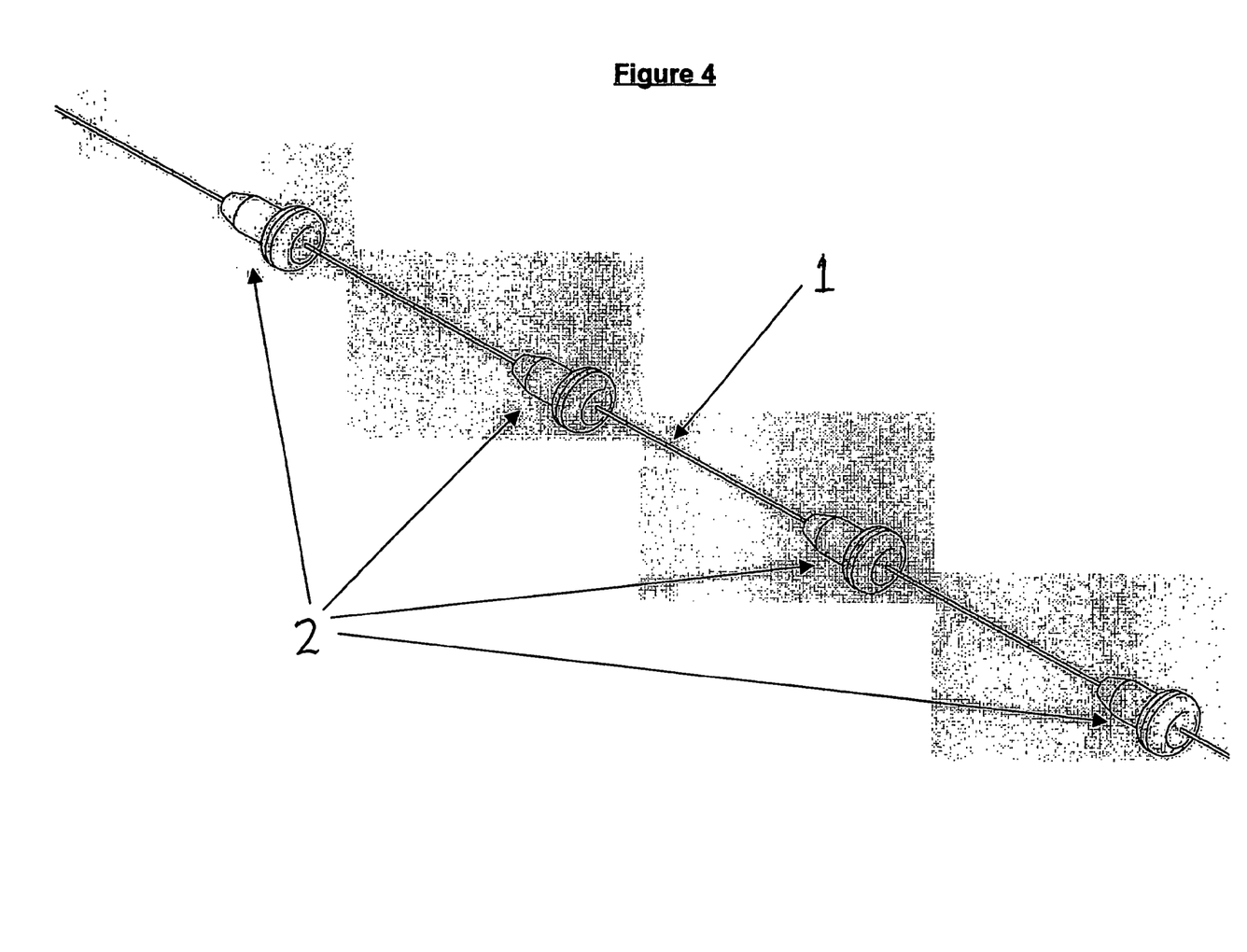
FIGS. 4 and 5 are a perspective view and cross-section respectively through a plurality of seals on a wire.
Figure 5:
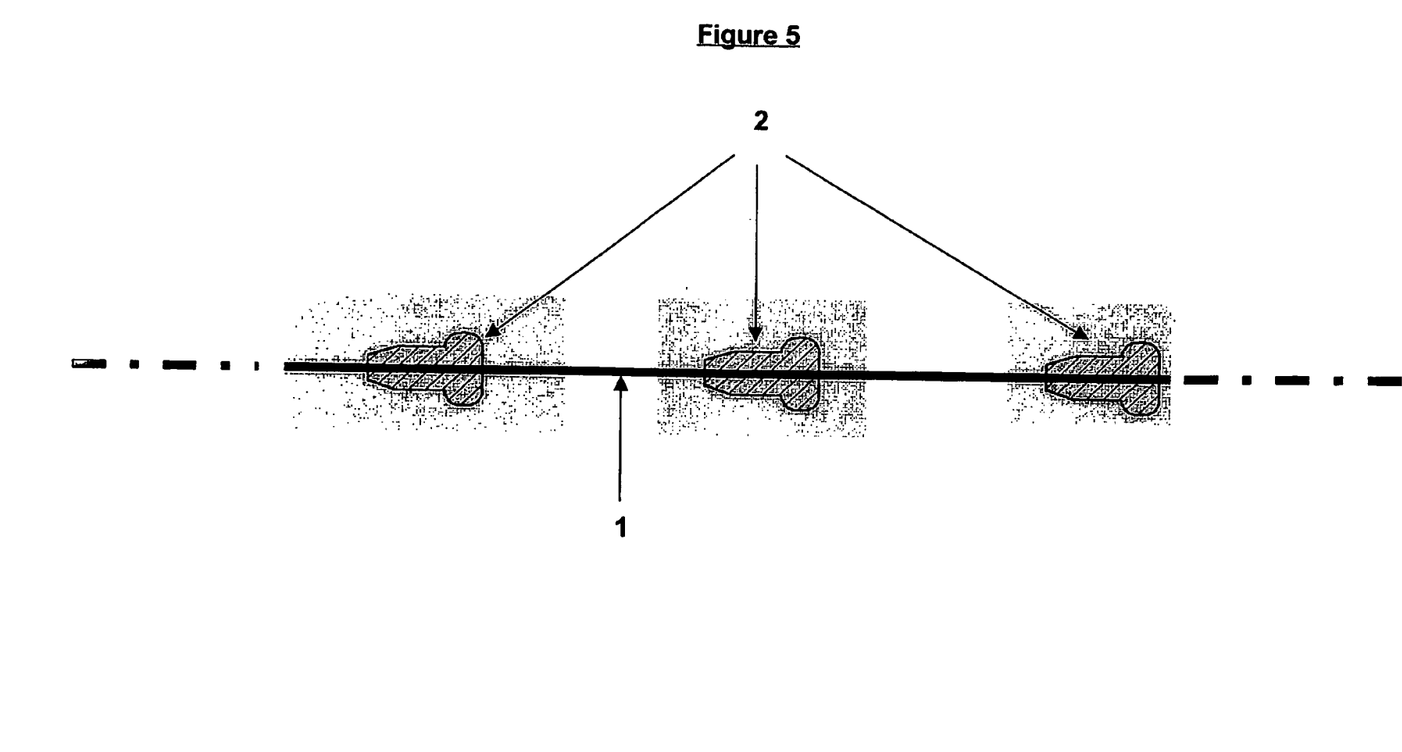

FIG. 3 shows a cross sectional detail of the current collector/seal area after closure of the casing. The electrode stack in the region where the current collector 1 exits aperture 12 in sensor body 3 has been omitted for clarity. The longitudinal compression provided by clip 8, together with the radial compression provided by insertion of the seal 2 into the aperture 12 provides the long sealing path between the current collector, sensor body and seal as shown.

The completed dimensions of the sensor are 17 mm wide by 17 mm deep by 4 mm high which is extremely compact in comparison with most commercial devices of comparable performance. This size reduction is, to a great extent, facilitated by a series of design choices which rely on the robust electrolyte seal as described by this invention.

Figure 6:
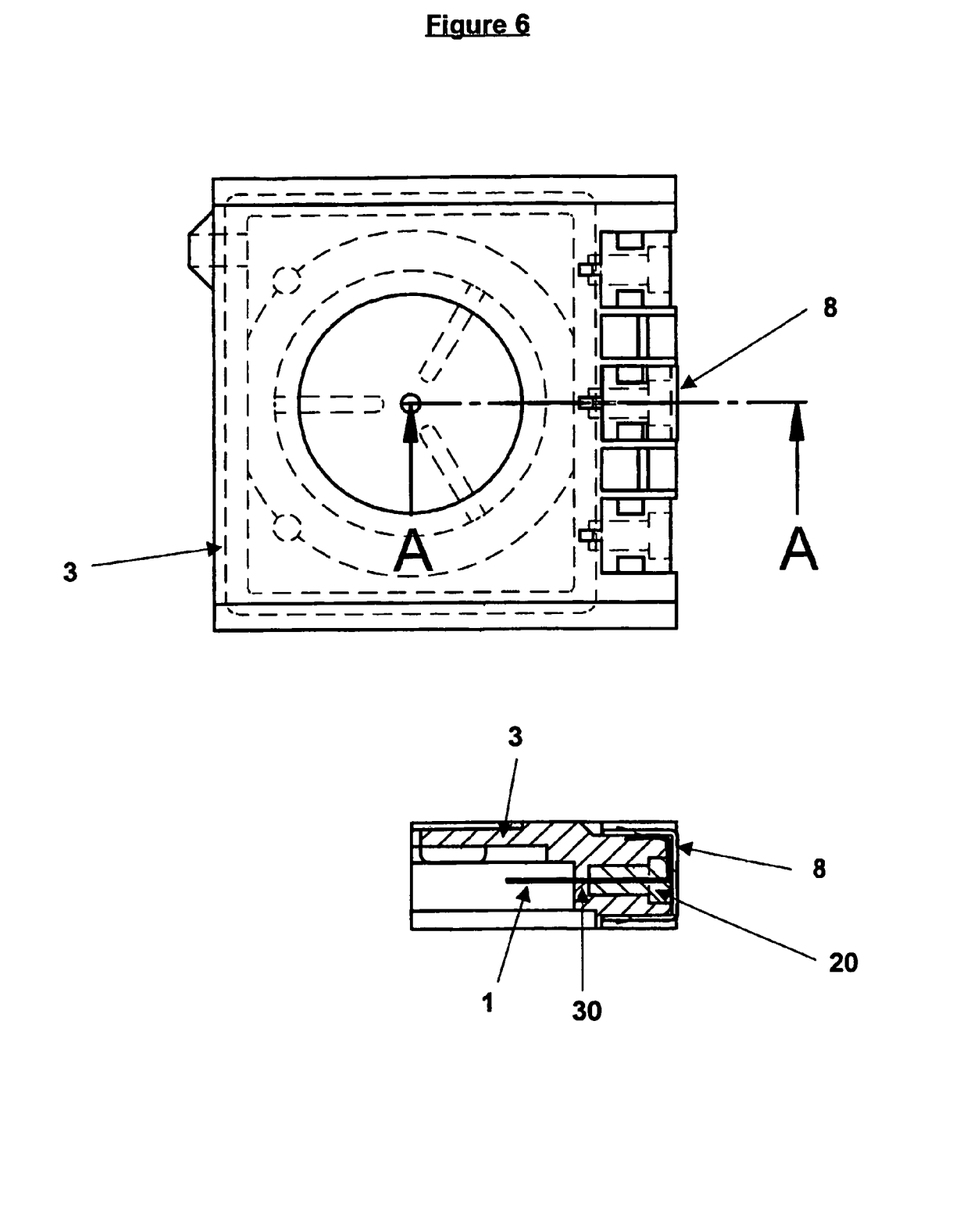
FIGS. 6(a) and 6(b) are a plan and section on A-A respectively of a second sensor of the invention

FIG. 6 illustrates a second example of a sensor in which the seal has been provided by the back-filling technique. The body 3, current collector 1 and clip 8 are all constructed (and perform the same functions) as previously described. However, in this case the current collector 1 is initially held in position by means 30. This can be achieved by moulding a short section of the current collector in to the main body, as shown here. The contact between current collector 1 and body 3 in the region of 30 does not necessarily form part of the electrolyte seal. Thus, the fact that body 3 is made from a relatively non-compliant material is not a drawback. Indeed, the characteristics of the material used to fabricate the body 3 in this case are to some extent dictated by the requirement that it should be able to withstand the temperatures and pressures which are generated during the back-filling process. Typical examples of materials which can be used in these applications are ABS and similar polymers for the body 3 and thermoplastic elastomers for the back-fill 20.

Alternatively, 30 may comprise a separate clip or other current collector locating means. In either case, the purposes of 30 are:

(a) to retain current collector 1 in position whilst the back-filling process takes place and (b) to seal the inner part of the seal cavity so preventing leakage of the back-filling material into the interior of the body.

Standard two shot injection moulding technology can be used to facilitate the back-filling in a single tool. Alternatively, the body/current collector assembly can be formed in a first tool and then transferred to a second tool where the back-filling process occurs. In either case, material 20 is injected into the cavity around current collector 1 and finally clip 8 is attached to complete the assembly. The back-filled material is left slightly proud so that it is compressed by application of the clip.

It is believed that the above described embodiments can be configured to be one quarter of the size of previously commercially viable electrochemical sensors.

It is emphasised that the insertion of the seals into the preformed apertures in the rigid sensor housing not only provides an excellent seal against electrolyte leakage during use; it also holds the current collectors in position relative to the case so that they can be folded down into the electrode stack at appropriate stages during the assembly process. The base closure does not require any additional alignment of the current collectors, as is the case when the electrolyte seal is produced by pressure applied by the overall housing closure. This improvement simplifies the sensor assembly, and, since automated insertion of the seal current collector assembly may be envisaged, removes one of the main obstacles, which has historically prevented machine assembly of sensors of this type.

The sealing technique employed in the preferred embodiments, in which the current collector exits through the body of the sensor (and in which the compliant tape stack perimeters are not a primary source of electrolyte retention), overcomes problems which are particularly challenging in the case of miniaturised sensors. However, many of the advantages offered by this method are applicable to larger sensors and the ability to redesign such devices to incorporate these improvements is a further benefit offered by the invention.

Figure 7:
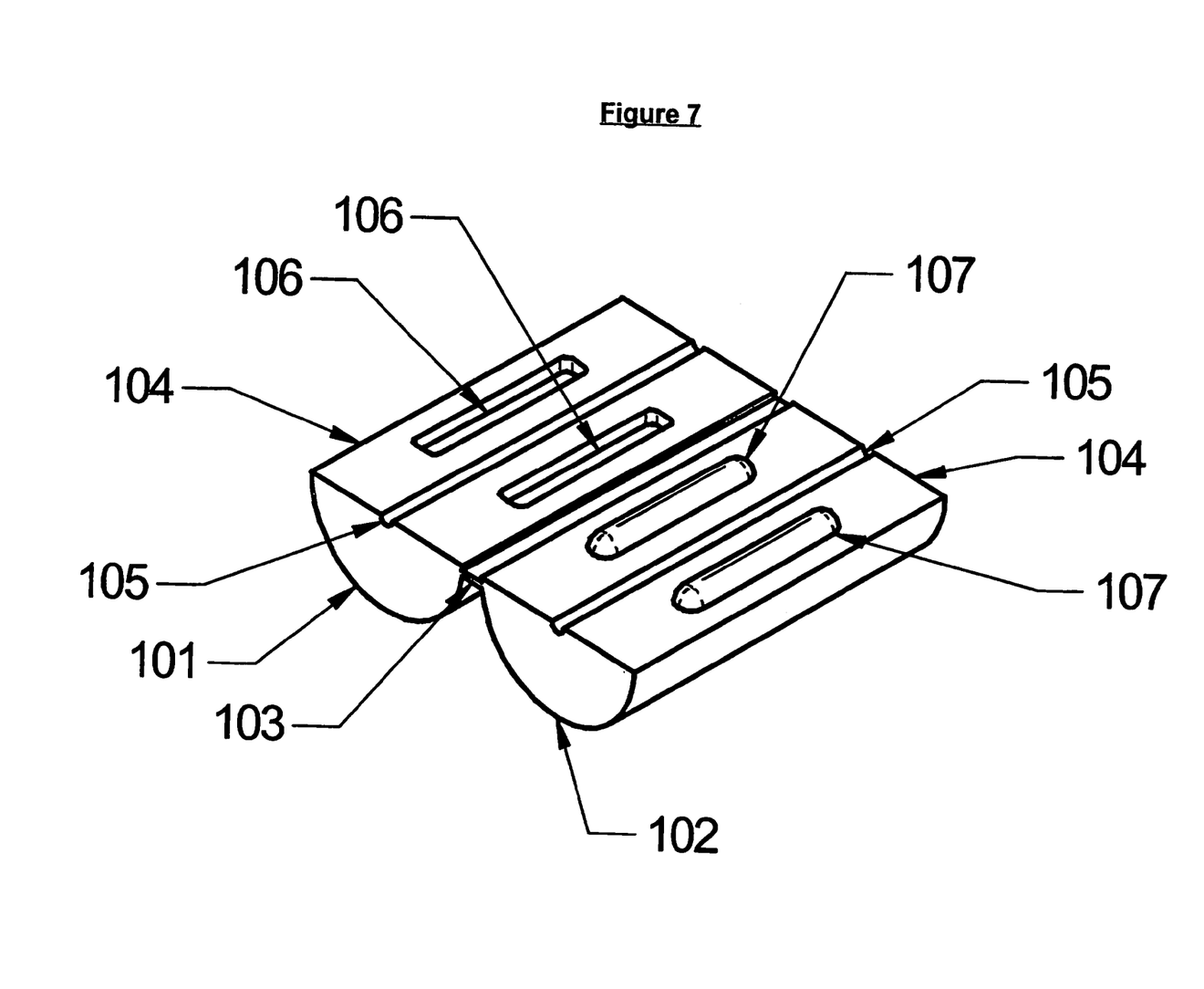
FIG. 7 shows in a perspective view an alternative moulding for a seal of the invention.

The invention is not intended to be restricted to the details of the above described embodiments. An alternative seal moulding is shown in FIG. 7. It is comprised of two "clam shell" halves 101,102 connected by a living hinge 103 (which can be dispensed with, the two halves being moulded separately). When the halves are hinged together, they form a seal of elliptical cross-section. Each half in its flat face 104 has a central groove 105 for receiving its current collector and a recess 106 on one side of the groove and a complementary rib 107 on the other side. These ensure that as the seal halves are closed together around the current collector, they mate in their intended position.

What is claimed is:

1. A current collector and a seal combination for an electrochemical sensor comprising:

a housing, a relatively flat reference, sensing, and counter electrodes within the housing, the relatively flat reference, sensing and counter electrodes are stacked vertically and centered about a common vertical axis and in contact with a liquid electrolyte;

a plurality of connection apertures arranged in a horizontal row extending along a wall of the housing directly adjacent corresponding edges of the reference, sensing and counter electrodes, the current collector and seal combination further comprising:

a plurality of relatively straight, flexible, metal current collectors, each of the plurality of current collectors extending through a respective connection aperture of the plurality of connection apertures to the vertically stacked reference, sensing and counter electrodes with an end of each current collector trapped against and in direct contact with the reference, sensing and counter electrodes;

a compliant seal of a thermoplastic elastomeric material over-molded directly onto each of the flexible metal current collectors, the compliant seal is inserted into one of the connection apertures, the current collector extending through the compliant seal;

the compliant seal being in contact with the current collector substantially throughout its length along the current collector; and an arrangement being such that compressive stress induced in the compliant seal by reaction from the connection aperture urges the compliant seal into distributed sealing contact with the current collector substantially through a length of the compliant seal.

2. The current collector and seal combination of claim 1, wherein the length of the compliant seal is longer than its outer diameter or other major cross-sectional dimension.

3. The current collector and seal combination of claim 2, wherein a ratio of the length of the compliant seal to the outer diameter is of an order of at least 3:1.

4. The current collector and seal combination of claim 1, claim 2 or claim 3, wherein a ratio of the length and/or the outer diameter of the compliant seal to a diameter of the current collector is at least of an order of 10:1.

5. The current collector and seal combination of claim 1, claim 2, or claim 3, wherein a ratio of the length of the compliant seal to a diameter of the current collector is at least of an order of 30:1.

6. The current collector and seal combination of claim 1, wherein the compliant seal is injection moulded as an overmoulding onto the current collector.

7. The current collector and seal combination of claim 1, wherein the compliant seal is molded with a central throughbore for threading of the current collector through the compliant seal.

8. The current collector and the seal combination of claim 1, wherein the compliant seal is molded with a slot, nick or notch, for introduction of the current collector into the compliant seal.

9. The current collector and seal combination of claim 1, wherein the compliant seal is moulded as two complementary halves having a central groove for receiving the current collector.

10. The current collector and seal combination of claim 1, wherein the compliant seal has one or more ridges extending around its outer circumference.

11. The current collector and seal combination of claim 1, wherein the compliant seal has a cylindrical body and a larger diameter outer end boss.

12. The current collector and seal combination of claim 1, wherein the compliant seal has a tapered nose.

13. An electrochemical gas sensor having:

a housing having at least one wall and a plurality of connection apertures arranged in a horizontal row extending along and through the wall, the connection apertures having bores directly adjacent corresponding edges of a relatively flat reference, sensing and counter electrodes, the relatively flat reference, sensing and counter electrodes are stacked vertically and centered about a common vertical axis in the housing, a liquid electrolyte contained in the housing in chemical contact with the electrodes, and a plurality of current collectors in electrical contact with respective ones of the respective electrodes;

the plurality of current collectors and respective electrodes are characterized in that:

the plurality of current collectors in combination with a corresponding plurality of compliant seals are arranged in accordance with the current collector and seal combination of claim 1;

wherein the current collectors extend within the compliant seals through respective ones of the connection apertures from the electrodes to outside the housing; and the compliant seals are in compression against both the current collectors and at least part of the bores of the connection apertures, wherein the current collectors provide means for electrical contact outside the housing and the connection apertures are sealed.

14. The electrochemical sensor of claim 13, wherein the compliant seal is an interference fit in the aperture.

15. The electrochemical sensor of claim 13, wherein the compliant seals have cylindrical bodies and larger diameter outer end bosses and the connection apertures have a complementary shape.

16. The electrochemical sensor of claim 13 including metallic end caps clipped to the housing and captivate the current collectors, thereby providing electrical connections for the electrochemical sensor.

17. An electrochemical gas sensor having:

a housing having at least one wall and a plurality of connection apertures arranged in a horizontal row extending along and through the wall, the connection apertures having bores directly adjacent corresponding edges of a relatively flat reference, sensing and counter electrodes, a relatively flat reference, sensing and counter electrodes are stacked vertically and centered about a common axis in the housing, a liquid electrolyte contained in the housing in chemical contact with the electrodes, and a plurality of current collectors in electrical contact with respective ones of the respective electrodes;

the plurality of current collectors and respective electrodes are characterized in that:

the plurality of current collectors in combination with a corresponding plurality of compliant seals are arranged in accordance with the current collector and seal combination of claim 1, wherein the current collectors extending through respective ones of the connection apertures from the electrodes to outside the housing;

the compliant seals are in compression against both the current collectors and at least part of the bores of the connection apertures; whereby the current collectors provide means for electrical contact outside the housing and the connection apertures are sealed;

the current collectors are preliminarily located in the connection apertures;

the compliant seals are back-fillings of sealing material into the connection apertures; and the back-fillings are compressed by end caps.

18. The electrochemical sensor of claim 17, wherein the end caps are metallic, clipped to the housing, and captivate the current collectors, thereby providing electrical connections for the electrochemical sensor.

19. The electrochemical sensor of claim 13, or claim 17, wherein an elastic moduli of the housing and of the compliant seal differ by at least two orders of magnitude, the housing being stiffer and the compliant seal being more compliant.

\* \* \* \* \*